United States Patent [19]
Bierre et al.

[11] Patent Number: 5,795,727
[45] Date of Patent: *Aug. 18, 1998

[54] GRAVITATIONAL ATTRACTOR ENGINE FOR ADAPTIVELY AUTOCLUSTERING N-DIMENSIONAL DATASTREAMS

[75] Inventors: Pierre Bierre, Redwood City, Calif.; Ronald A. Mickaels, Moutain View, Calif.

[73] Assignee: Becton Dickinson and Company, Fraklin Lakes, N.J.

[*] Notice: The term of this patent shall not extend beyond the expiration date of Pat. No. 5,627,040.

[21] Appl. No.: 643,669

[22] Filed: May 6, 1996

Related U.S. Application Data

[63] Continuation of Ser. No. 039,465, Apr. 26, 1993, Pat. No. 5,627,040, which is a continuation-in-part of Ser. No. 751,020, Aug. 28, 1991, abandoned.

[51] Int. Cl.$^6$ .................. G01N 33/533; G01N 33/49; G01N 33/536
[52] U.S. Cl. .................. 435/7.24; 436/536; 436/172; 436/800; 436/805; 302/133; 302/134
[58] Field of Search .................. 435/7.24, 806; 436/172, 800, 805, 536; 382/133, 134

[56] References Cited

U.S. PATENT DOCUMENTS

| | | | |
|---|---|---|---|
| 4,599,307 | 7/1986 | Saunders, et al. | 435/34 |
| 4,661,913 | 4/1987 | Wu, et al. | 364/500 |
| 4,704,891 | 11/1987 | Recktenwald, et al. | 73/1 |
| 4,727,020 | 2/1988 | Recktenwald, et al. | 73/1 |
| 4,745,285 | 5/1988 | Recktenwald, et al. | 250/458.1 |
| 4,805,225 | 2/1989 | Clark | 382/15 |
| 4,965,725 | 10/1990 | Rutenberg | 364/413.1 |
| 4,987,086 | 1/1991 | Brosnan, et al. | 436/501 |
| 5,017,497 | 5/1991 | de Grooth, et al. | 436/63 |
| 5,041,733 | 8/1991 | Noguchi, et al. | 250/461.2 |
| 5,144,224 | 9/1992 | Larsen | 324/71.4 |
| 5,627,040 | 5/1997 | Bierre et al. | 437/7.24 |

OTHER PUBLICATIONS

Bezdek, James C. and Chiou, Er–Woon–"Core Zone Scatterplots: A New Approach to Feature Extraction for Visual Display;" Computer Vision, Graphics, and Image Processing 41, 186–209 (1988).

Egbert, et al., IEEE Conf. Neural Networks, pp. 561–88 (1988).

Imasoto, et al., Toshiba Review, (1975).

Lippman, IEEE ASSP Magazine, "An Introduction to Computing with Neural Nets", pp. 4–21 (1987).

Frankel, et al., "Use of a Neural Net Computer System for Analysis of Flow Cytometric Data of Phytoplankton Populations," Cytometry, pp–540–550(1989).

*Primary Examiner*—Lora M. Green
*Attorney, Agent, or Firm*—Eric M. Lee; Allen W. Wark

[57] ABSTRACT

This invention relates to a method for autoclustering N-dimensional datastreams. The invention has particular utility in analyzing multi-parameter data from a flow cytometer, and more particularly has utility in analyzing data from whole blood cells tagged with fluorescently labelled CD3, CD4 and CD8 monoclonal antibodies to which a known number of fluorescent microbeads has been added.

13 Claims, 6 Drawing Sheets

GRAVITATIONAL ATTRACTOR ENGINE FOR ADAPTIVELY AUTOCLUSTERING N-DIMENSIONAL DATASTREAMS

This is a continuation of application Ser. No. 08/039,465, filed Apr. 26, 1993, now U.S. Pat. No. 5,627,040, which is a continuation-in-part of U.S. Ser. No. 07/751,020, filed Aug. 28, 1991, now abandoned.

FIELD OF THE INVENTION

This invention relates to a method for classifying multi-parameter data in real time (or from recorded data) into cluster groups for the purpose of defining different populations of particles in a sample. This invention is particularly useful in the field of flow cytometry wherein multi-parameter data is recorded for each cell that passes through an illumination and sensing region. It is especially useful for classifying and counting immunofluorescently labeled CD3, CD4 and CD8 lymphocytes in blood samples from AIDS patients.

BACKGROUND OF THE INVENTION

Particle analysis generally comprises the analysis of cells, nuclei, chromosomes and other particles for the purpose of identifying the particles as members of different populations and/or sorting the particles into different populations. This type of analysis includes automated analysis by means of image and flow cytometry. In either instance, the particle, such as a cell, may be labeled with one or more markers and then examined for the presence or absence of one or more such markers. In the case of a cell, such as a leukocyte, tumor cell or microorganism, the marker can be directed to a molecule on the cell surface or to a molecule in the cytoplasm. Examination of a cell's physical characteristics, as well as the presence or absence of marker(s), provides additional information which can be useful in identifying the population to which a cell belongs.

Cytometry comprises a well known methodology using multi-parameter data for identifying and distinguishing between different cell types in a sample. For example, the sample may be drawn from a variety of biological fluids, such as blood, lymph or urine, or may be derived from suspensions of cells from hard tissues such as colon, lung, breast, kidney or liver. In a flow cytometer, cells are passed, in suspension, substantially one at a time through one or more sensing regions where in each region each cell is illuminated by an energy source. The energy source generally comprises an illumination means that emits light of a single wavelength such as that provided by a laser (e.g., He/Ne or argon) or a mercury arc lamp with appropriate filters. Light at 488 nm is a generally used wavelength of emission in a flow cytometer having a single sensing region.

In series with a sensing region, multiple light collection means, such as photomultiplier tubes (or "PMT"), are used to record light that passes through each cell (generally referred to as forward light scatter), light that is reflected orthogonal to the direction of the flow of the cells through the sensing region (generally referred to as orthogonal or side light scatter) and fluorescent light emitted from the cell, if it is labeled with fluorescent marker(s), as the cell passes through the sensing region and is illuminated by the energy source. Each of forward light scatter (or FSC), orthogonal light scatter (SSC), and fluorescence emissions (FL1, FL2, etc.) comprise a separate parameter for each cell (or each "event"). Thus, for example, two, three or four parameters can be collected (and recorded) from a cell labeled with two different fluorescence markers.

Flow cytometers further comprise data acquisition, analysis and recording means, such as a computer, wherein multiple data channels record data from each PMT for the light scatter and fluorescence emitted by each cell as it passes through the sensing region. The purpose of the analysis system is to classify and count cells wherein each cell presents itself as a set of digitized parameter values. Typically, by current analysis methods, the data collected in real time (or recorded for later analysis) is plotted in 2-D space for ease of visualization. Such plots are referred to as "dot plots" and a typical example of a dot plot drawn from light scatter data recorded for leukocytes is shown in FIG. 1 of U.S. Pat. No. 4,987,086. By plotting orthogonal light scatter versus forward light scatter, one can distinguish between granulocytes, monocytes and lymphocytes in a population of leukocytes isolated from whole blood. By electronically (or manually) "gating" on only lymphocytes using light scatter, for example, and by the use of the appropriate monoclonal antibodies labeled with fluorochromes of different emission wavelength, one can further distinguish between cell types within the lymphocyte population (e.g., between T helper cells and T cytotoxic cells). U.S. Pat. Nos. 4,727,020, 4,704,891, 4,599,307 and 4,987,086 describe the arrangement of the various components that comprise a flow cytometer, the general principles of use and one approach to gating on cells in order to discriminate between populations of cells in a blood sample.

Of particular interest is the analysis of cells from patients infected with HIV, the virus which causes AIDS. It is well known that $CD4^+$ T lymphocytes play an important role in HIV infection and AIDS. For example, counting the number of $CD4^+$ T lymphocytes in a sample of blood from an infected individual will provide an indication of the progress of the disease. A cell count under 400 per $mm^3$ is an indication that the patient has progressed from being seropositive to AIDS. In addition to counting $CD4^+$ T lymphocytes, $CD8^+$ T lymphocytes also have been counted and a ratio of CD4:CD8 cells has been used in understanding AIDS.

In both cases, a sample of whole blood is obtained from a patient. Monoclonal antibodies against CD3 (a pan-T lymphocyte marker), CD4 and CD8 are labeled directly or indirectly with a fluorescent dye. These dyes have emission spectra that are distinguishable from each other. (Examples of such dyes are set forth in example 1 of U.S. Pat. No. 4,745,285.) The labeled cells then are run on the flow cytometer and data is recorded. Analysis of the data can proceed in real time or be stored in list mode for later analysis.

While data analyzed in 2-D space can yield discrete populations of cells, most often the dot plots represent projections of multiple clusters. As a result, often it is difficult to distinguish between cells which fall into regions of apparent overlap between clusters. In such cases, cells can be inadvertently classified in a wrong cluster, and thus, contribute inaccuracy to the population counts and percentages being reported. In blood from an HIV infected patient for example, over-inclusion of T cells as being $CD4^+$ could lead a clinician to believe a patient had not progressed to AIDS, and thus, certain treatment which otherwise might be given could be withheld. In cancers, such as leukemia, certain residual tumor cells might remain in the bone marrow after therapy. These residual cells are present in very low frequencies (i.e., their presence is rare and thus their occurrence in a large sample is a "rare event"), and thus, their detection and classification are both difficult and important.

Current data analysis methods fail to provide sufficient means to discriminate between clusters of cells, and thus, fail to permit more accurate identification and/or sorting of cells into different populations. In addition, such methods fail to predict if the preparative conditions used by the technician were done properly (e.g., improper staining techniques leading to non-specific staining or pipetting improper amounts of reagent(s) and/or sample(s)). Finally, most methods work well for mononuclear preparations from whole blood or on erythrocyte lysed whole blood but perform poorly on unlysed whole blood because of the over abundance of red cells and debris in a sample.

SUMMARY OF THE INVENTION

The autoclustering method, described herein as the "gravitational attractor engine", addresses the need to automatically assign classifications to multi-parameter events as they arrive from an array of sensors such as the light collection means of a cytometer. It also functions in the post-classification of recordings of multi-parameter events in list-mode or database format. It is particularly useful in clustering Z-parameter data from CD3 and CD4 as well as CD3 and CD8 T cells labeled with immunofluorescent markers in blood samples from AIDS patients.

The gravitational attractor consists of a geometric boundary surface of fixed size, shape and orientation, but of variable position, a computational engine by which the boundary surface positions itself optimally to enclose a cluster of multi-parameter events. Multiple attractors may be employed simultaneously for the purposes of classifying multiple clusters of events within the same datastream or recorded data distribution, the strategy being to assign one attractor per population to be identified and/or sorted. Classification of events in the datastream consists of a two-step process: In the first step (pre-analysis), the datastream is analyzed for purposes of precisely centering each attractor's membership boundary surface about the statistical center-of-mass of the data cluster (i.e., population) it is intending to classify. Pre-analysis is terminated after a pre-determined number of events have been analyzed or if insignificant deviations in an attractor position is found. In the second step (classification), each attractor's membership boundary is "locked down in place", and incoming datastream events are tested against membership boundaries for classification inclusion vs. exclusion.

Major benefits of the gravitational attractor engine are that it: 1) requires no list-mode recording of events in the process of their classification (i.e., data may be analyzed in real time); 2) provides a classification method tolerant of between-sample drift in the central value of a data cluster which may arise from any arbitrary combination of instrumentation, sample-preparation and intrinsic sample variance sources; 3) exhibits stability in the case of multiple missing clusters and can count particles in a population down to absolute zero in the vicinity of where the cluster is expected to locate; and 4) provides continuous access to population vector means and membership counts during sampling of the datastream, allowing continuous process quality assurance (or "PQA") during time-consuming, rare-event assays.

Several extensions to the gravitational attractor engine increase its benefits: 1) hyperspherical boundary surfaces can be elongated on a preferred axis to obtain a cigar-shaped attractor; 2) the boundary surface used to gate events for gravitational interaction during pre-analysis can be different in shape and extent from the membership boundary applied during classification; and 3) the subset of parameters used to cluster events can be different for different attractors, allowing smear-inducing parameters to be ignored and permitting data classification at varying degrees of dimensional collapse.

The primary advantage of the gravitational attractor engine is its capacity for accurate and efficient autoclustering, that is, it can replace manual-clustering methods which require human judgment to adapt gating geometry to normal variances in the positions of target clusters. By comparison, prior autoclustering methods which rely on histogram curve analysis to locate threshold-type separators are less-robust in the handling of missing populations (especially multiple missing clusters).

A cigar-shaped attractor engine performs well at classifying diagonally-elongated clusters whose "stretch" originates from partially-correlated (i.e., uncompensated) events. By comparison, prior methods utilizing 1-D histogram analysis do not work as well with uncompensated clusters because their 1-D histogram projections consume excessive curvespace. Since an attractor can be defined in arbitrary N-dimensional space, the problem of overlapping clusters may be redressed through the addition of extra parameters to tease them apart at no additional computational complexity. The simplicity and highly parallel nature of the attractor engine's computations, together with its stream-oriented data interaction, makes this autoclassification method ideally suited to real time classification performed on high-event rate, multi-parameter datastreams. Compared to prior methods which require remembering a list-mode recording in order to perform data analysis, the attractor engine's memory requirements are small and unrelated to the datastream length being sampled, thus making practicable routine analyses in which several million events are sampled. The salient benefit of such mega-assays in cellular diagnostics is to detect diseased cells at thresholds as low as 1 per million normal cells (i.e., rare-event assays), thus, enabling earlier detection and milder interventions to arrest disease.

DESCRIPTION OF THE DRAWINGS

The file of the patent includes at least one drawings executed in color.

FIGS. 1A and 1B depict two such projective scatterplots (5 and 6), showing the spherical attractor's centroid (1), radius (2) and orbital band (7), and the cigar attractor's centerline (3), radius (4) and orbital band (8).

DETAILED DESCRIPTION

Figure 1A:
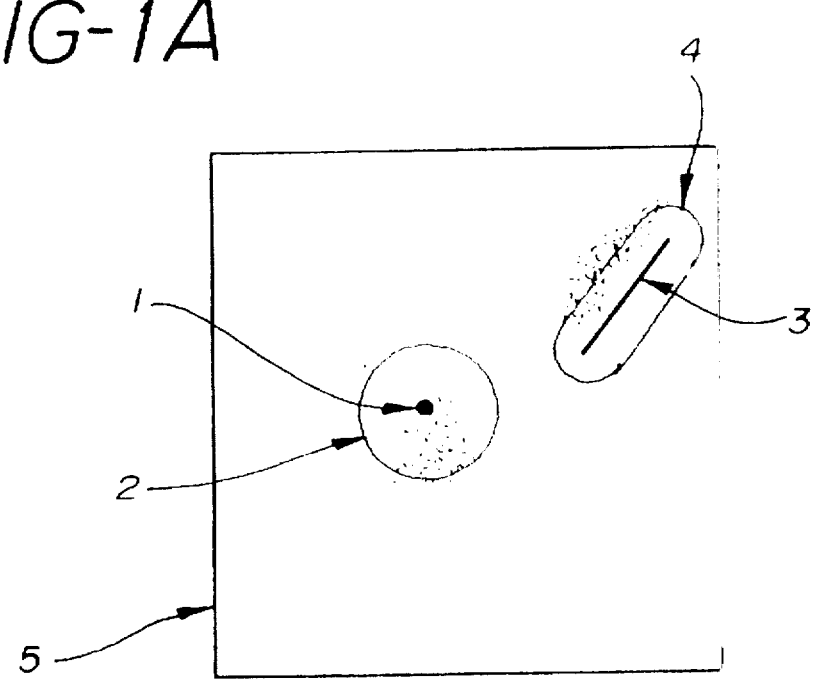
FIGS. 1A and 1B illustrate two multi-dimensional attractors (one spherical and one cigar-shaped) at their seed locations in multi-space prior to pre-analysis.

A gravitational attractor is a small computational "engine". Initially, it contains one or more geometric parameters set by the user for each type of sample to be analyzed or fixed to define an expected target cluster's shape, size and approximate location. The attractor engine further comprises a method for locating a cluster's actual center-of-mass in the datastream being analyzed, and to subsequently classify events in the arriving datastream which satisfy the attractor's geometric membership predicate. The term "gravitational" is apt because the attractor finds its optimal location enclosing the data cluster by falling to its center-of-mass location under the accumulative gravitational force of events in proximity to its expected location in multi-space. The term "attractor", drawn from dynamical systems theory, refers to the behavior of a system whereby a multitude of initial state vectors move toward, and converge upon a common, equilibrium end-state vector. In this case, the state vector corresponds to the instantaneous vector location of a roving geometric boundary surface (specifically a rigidly-attached reference point within it), as the boundary moves from an initial, expected "seed" location to equilibrium at a data cluster's actual center-of-mass location.

The gravitational attractor described below illustrates the simplest case of membership geometry, the hypersphere. The engine of a spherical attractor comprises the following fixed and variable components:

| Fixed components: | s | seed, or initial centroid vector of hypersphere representing approximate expected location of cluster |
|---|---|---|
| | r | radius of hypersphere |
| variable components: | c | current centroid vector of hypersphere |
| | n | number of gravitationally-interacting events so far within the current datastream |

Before a datastream begins, the invariant aspects of the target cluster are first specified in terms of seed location, s, and radius, r. The specifications of S and r are made by observing projections of the cluster in 2-D projection scatterplots, whereby two coordinates of s are adjusted at a time using an 2-D locator device, and r is edited by "pulling" on its appearance with a locator device until satisfactory.

The events in the datastream encountered consist of a variable number of multi-parameter events $e_i$ where i indexes the number (or sequence) of the event in the stream and e is the vector of parameter values comprising that particular event. Prior to analyzing the datastream, c is initialized to the seed location, s.

Attractor autoclustering of the datastream comprises a two-step process: In the first step, pre-analysis, the datastream is analyzed for purposes of precisely centering the attractor's membership boundary surface about the statistical center-of-mass of the data cluster it is intending to classify. Upon arrival of the first event, and that of each subsequent event during pre-analysis, the spherical attractor transforms each event vector into its own local coordinate system, whose origin is based at c:

local $e_i = e_i - c$ (transformation to local coordinates)

Next, the attractor decides whether local $e_i$ is short enough in length ($e_i$ is close enough in proximity to c) to be allowed attractive pull on c. The interaction gating predicate, g, evaluates affirmatively if local $e_i$ has vector length less than r:

g (local $e_i$)=length (local $e_i$)<r

If the above proximity test is met, $e_i$ is permitted to exert an increment of attractive pull on c (i.e., to enter into the center-of-mass calculation). The center-of-mass of a lone cluster in an otherwise vacuous dataspace can be defined simply as the vector-mean of all N event vectors, $e_i$:

$c = \Sigma e_i / N$ (center-of-mass for lone cluster)

In multi-cluster distributions, each cluster applies its interaction gating function, g, whose job is to protect its centroid calculation from the influence of density pockets elsewhere in space:

$c = \Sigma e_i * g$ (local $e_i$) /N

Rather than update c continuously with each interaction (an inefficient approach prone to instability the case of missing clusters), the attractor's centroid, c, is updated on a fixed schedule at prescribed interaction count milestones (i.e., s1, s2, s3 ... sm). For this purpose, the attractor keeps a running vector sum sigma of all its interacting event vectors. At the start of pre-analysis, sigma and n are zeroed. During pre-analysis, each arriving event vector which satisfies the above gating predicate is accumulated, by vector addition, into sigma, the interaction count n is incremented, sigma=sigma+$e_i$ (effect of each event interaction)

n=n+1 and if n is one of the scheduled update milestones (e.g., S1) the centroid is updated c=sigma/n (effect of centroid update)

whereby the new value of c is the running vector sum sigma, scalar divided by n. At the completion of each update, c contains the vector mean of all events which have so far interacted with the attractor. This new, refined value of c, which carries the weight of more data than did the its previous value, governs subsequent interaction gating until the next update milestone is reached.

The initial seed point, s, serves as a default centroid to get the calculation started. It should reflect the best available information about expected cluster position. Once the gated vector sum has accumulated some actual data (e.g., s1=50), the computed centroid, c, replaces s as the best-available central value for anchoring the interaction gate.

local $e_i = e_i - c$ (computed c replaces s)

The update schedule for c subserves the goal of only improving its accuracy over time. The first attractor update milestone s1 is called the threshold of inertia. It must be overcome in order to replace the seed value s, as a check on wandering. If a cluster were depleted down to a handful of events, and the centroid were allowed to update on the first gated event, and that event fell just inside the gate, the updated gate could be dislocated up to a distance r from the seed point, possibly excluding centrist events from further consideration. If the threshold of inertia cannot be surmounted, no positional refinement is allowed (i.e., the seed value, s, specifies default emplacement of cluster membership geometry). Consequently, clusters which have become so depleted that no density landmark can be established are default-gated about the point where they were expected to have been found.

If the threshold of inertia can been surmounted, the attractor is allowed to gravitate toward the local center-of-mass. Periodic centroid updates (e.g., every 50 interactions) would move the attractor toward a convergence point, but a more efficient update schedule observes the statistical rule that residual error diminishes as the inverse square root of the number of interactions. Therefore, a parabolic update schedule (e.g., s1=100, s2=400, s3=900, s4=1600 . . . ) provides statistically significant centroid corrections on every update, whereas periodic updates take the centroid along a more oscillatory path toward the same eventual outcome.

The cessation of the pre-analysis activity for a single attractor is triggered by either attainment of the number of interactions, sm, specified as the final scheduled update milestone (the attractor's "interaction quota"), or a global time-out metered in time or total events acquired, which ever comes first. If multiple attractors are interacting with the pre-analysis datastream, attractors which have reached their interaction quotas lay dormant while awaiting the attainment of quota by all other attractors, or the global time-out, whichever comes first. If pre-analysis is terminated by global time-out, each attractor which fell short of its interaction quota but which surpassed its threshold of inertia is given a final centroid update, so that event interactions accumulated since its last previous update are represented in the final value of the centroid, c. The specification of a global time-out, as a function of time or total acquired events, is necessary to guarantee termination of datastream pre-analysis unless there are apriori guarantees of sufficient population, for each target cluster in each datastream sample to always guarantee termination by satisfaction of interaction quotas.

Attractor-based autoclustering is a 2-step process. In the second step, "classification", each attractor's hyperspherical membership boundary is locked down in place at its centroid, c, frozen after the last pre-analysis centroid update was completed (or at s if no update took place). As each subsequent incoming event arrives in the continuation of the same datastream which was pre-analyzed, the incoming event is tested against each membership boundary for classification inclusion vs. exclusion, and a membership count incremented at each inclusion decision. If multiple classification and counting of the same event is unnatural or undesirable, one provides a contention resolving mechanism to assure that each event is classified and counted but by one attractor. A straightforward mechanism is to prioritize competing classifications, another is to award membership based on closest Euclidean proximity. One distinct advantage of prioritized classifications is that it can easily extend to attractors with more complex geometry's which can overlap in more complex ways, and for this reason it has been adopted into practice.

During classification, the membership count so far accumulated by each attractor is available for deciding when enough target events have been counted to terminate the assay. These accretional counts may be used for early detection of missing clusters, for example, indicating a sample-preparation omission which is cause for aborting the assay.

The cessation of classification is triggered by attainment of "membership quotas" for all attractors, or a global time-out expressed in time or total acquired events during the classification phase.

Both during and after the classification phase, each attractor holds its cluster population count and centroid (location) vectors, and thus, provides additional benefits to data analyses. Such benefits include quality-assurance mechanisms by which the user can define acceptable vs. aberrant datastream distributions, and automatically have the latter flagged.

A "minimum expected population" (defined apriori for each cluster as a function of membership count or a derivative thereof) is compared to the actual membership counts (or a derivative thereof) during, and after termination of, classification. An error condition or warning is generated for each cluster evidencing an unexpectedly low population. This type of PQA benefits from the unique missing cluster stability of the gravitational attractor classification method (i.e., the attractor will accurately count down to absolute zero the occurrence of events in the vicinity where the cluster was expected to have presented itself). A check on attainment of minimum expected population per each target cluster makes the overall autoclustering system vigilant to any number of instrumentation, sample preparation, and intrinsic sample aberration that express as absent target populations).

As a second benefit, a "tether" may be employed to define the permissible roving distance of each attractor from its seed position. A tether length (defined apriori and expressed as a scalar distance in multi-space) is compared to the actual displacement of c from its starting seed location, s, to determine if the tether length has been exceeded. If exceeded, an error or warning is generated indicating that a cluster has been found too far from its expected location. A test on proximity of actual cluster (vector mean) location to expected cluster location, per each target cluster, makes the overall autoclustering system vigilant to any number of instrumentation, sample preparation, and intrinsic sample aberration that express as unreasonable displacements in multi-space cluster location.

Though other classification methods can yield a population vector mean (and can compare proximity to apriori expected location), the attractor method has the unique advantage of requiring no list-mode recording. Because the tether constraint can be checked each time the attractor moves its position during pre-analysis, it is practical to detect cluster position aberrance early in exposure to the datastream, thus a time-consuming mega-assay can be interrupted early on, rather than waiting until its completion to find out it must be rejected for PQA reasons.

As a third benefit, a well formal cluster should consist of a dense area of events surrounded by a void region. To assure proper cluster membership and classification where a cluster is less well formed, an orbital band can be placed around the cluster membership boundary. The purpose of the orbital band is to guard against the movement of a cluster too far from its boundary, an unexpected change in the shape of a cluster and higher than expected noise. In any or all of such situations, a high number of events within the orbital band (or "orbiters") is an indication that the data may be unacceptable. Generally, less than 3% of ten events for a cluster should fall within the orbital band.

Figure 1B:
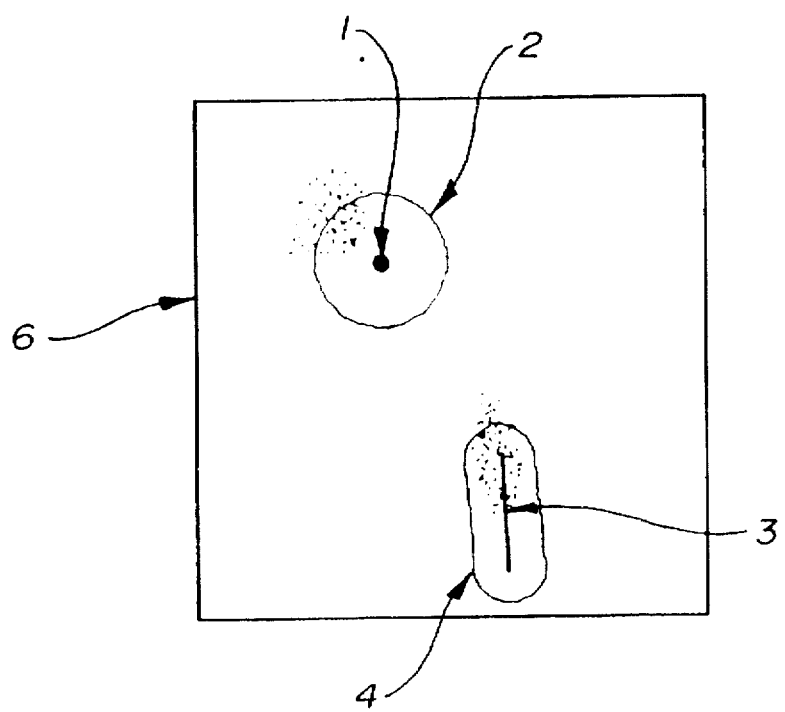
Figure 2A:
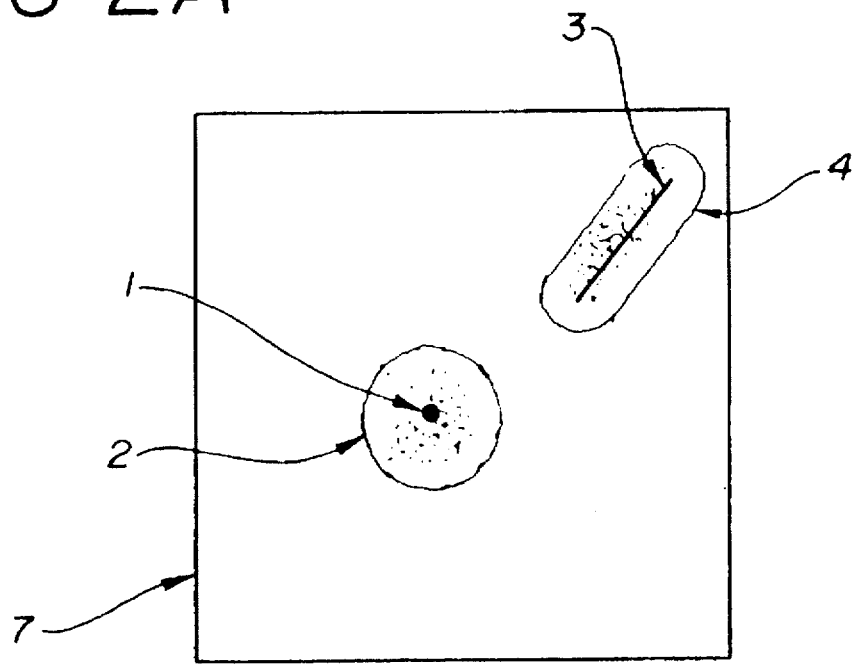
FIGS. 2A and 2B illustrate the same two attractors, by the same projection scatterplots, at their center-of-mass locations in multi-space during classification.
Figure 2B:
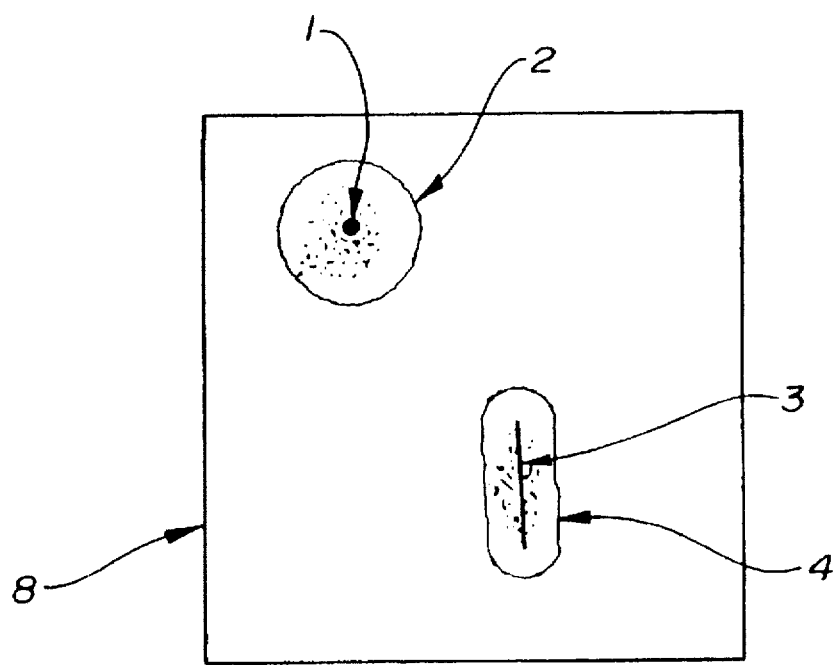

Referring to FIGS. 1A and 1B, the centroid (1), radius (2) and orbital band (2) are shown for a spherical attractor. The thickness of the orbital band is arbitrary. A "thin" band will include fewer orbiters than a "thick" band. FIGS. 2A and 2B show the movement of all of the components during classification.

A limitation of the hyperspherical attractor (i.e., it's not being well-fitted to the elongated shape of many multispace data clusters) can be overcome by a modification to the gating (or boundary surface) geometry. The characteristic of the attractors, whereby each employs an interaction gating function, g whose job is to protect its centroid calculation from the influence of events in other clusters, makes it advantageous to deploy gating geometries that closely approximate actual cluster shape. Better fitting boundaries allow the targeting of more populations within a fixed-size dataspace.

An adaptation that elongates the spherical attractor is to replace its centroid vector, c, with a straight line segment in multi-space running between two endpoint vectors, $e_1$ and $e_2$. The line connecting the two endpoints is called the attractor's "centerline". Instead of measuring the proximity of an event in terms of its distance from a single centerpoint, by extension, proximity is measured in terms of distance from the nearest point on the centerline. The locus of points equidistant from the centerline gives rise to a boundary surface that is a hypercylinder with rounded ends. In 3-D space, this solid assumes the shape of a cigar.

The cigar attractor's radius, cr, specifies both the cigar's cylindrical radius and the radius of curvature of its endcaps.

The midpoint, mp, of the centerline is the center of the cigar, and serves as the origin of the cigar's local coordinate system.

The geometric components of the cigar attractor that differ from those of the spherical attractor are:

| Fixed components: | | seed centerline = $[e_1s, e_2s]$ seed endpoints of initial centerline of cigar representing approximate expected location and orientation of cluster |
|---|---|---|
| | cr | radius of cigar cylinder and endcaps |
| variable components: | | centerline = $[e_1, e_2]$ current endpoints |
| | mp | midpoint of current centerline |

The cigar attractor's interaction gating function $g(e_i)$ for event $e_i$ is:

$g(e_i)$=distance($e_i$, centerline)<cr

The distance function first finds p, the nearest point on centerline to $e_i$ (the projection of $e_i$ onto centerline). If p projects beyond the end of the centerline, the distance to the closest endpoint is computed, otherwise the distance between the p and $e_i$ is used.

When the cigar attractor commences an update of its location during pre-analysis, the new midpoint mp assumes the value of the gated vector mean of all events which have thus far interacted. The endpoints of the centerline, maintaining rigid values in local coordinates, receive the same delta vector as was applied to mp, thus the centerline moves as a rigid structure under the pull of combined gravitational event force on its midpoint.

The cigar membership gating function applied during classification is the same as $g(e_i)$ above.

The proximity function and centerline update are the only aspects of the cigar attractor that differ from the spherical attractor. All other behaviors are identical. A primary benefit of the cigar attractor is its ability to handle correlated multi-parameter clusters. If two sensory channels are identical in their sensitivity and fed the same signal, all their 2-D event vectors will fall on the diagonal characterized by the equation (x=y). If two sensory channels have partially-overlapping sensitivities and are exposed to each other's uncorrelated input signals, the joint distribution will retain some diagonal stretch by virtue of unintended channel-crosstalk (uncompensated data). Electronic compensation (the subtracting out of cross talk components) is difficult to specify as the number of sensory channels and cross-talk interactions increases. A more practical approach, reduced to practice in this invention, is to cluster directly on raw, uncompensated event vectors employing a cigar attractor oriented along the principal stretch vector of the cluster in multi-space. The specification of the centerline endpoints is made by observing projections of the cluster in 2-D projection scatterplots, whereby two coordinates of the endpoint are adjusted at a time using an 2-D locator device. The specification of cr is edited by "pulling" on its appearance with a locator device until satisfactory.

Referring to FIGS. 1A and 1B, the center (3), radius (4) and orbital bands are shown for a cigar attractor. FIGS. 2A and 2B show the movement of these components during classification.

A slightly different geometry (other than cigar-shaped) suitable for elongated clusters is the hyperellipse. The attachment of an elliptical boundary surface to the attractor behavior claimed herein will be referred to as the elliptical attractor.

The orientation axis of the ellipse is specified by its two foci vectors $f_1$ and $f_2$. The proximity of an event is measured in terms of the sum of its two Euclidean distances from the two foci, and the ellipse radius, er, specifies the upper limit of this sum for the event inclusion.

The elliptical attractor's interaction gating function, $g(e_i)$ for event $e_i$ is:

$g(e_i)$=distance ($e_i$, $f_1$)+distance ($e_i$, $f_2$)<er

The midpoint, mp, of the orientation axis is the center of the ellipse, and serves as its local coordinate system origin. The specification of the principal axis and the gating function are the only two aspects of the elliptical attractor that differentiate it from the cigar attractor. As in the case of the cigar attractor, positional deltas applied to the midpoint propagate to each foci so that the ellipse can maintain its fixed orientation, size and shape.

The purpose of an attractor's classification geometry is to suitably enclose its target cluster's event cloud when deployed at its center-of-mass. The purpose of its interaction geometry is to define a "seek area" in which the attractor can expect to find its cluster (and little else). Since these two geometry's serve differing purposes, it is sometimes advantageous to customize the geometry's subserving interactions and classifications.

A spherical attractor may employ a "membership radius" different from its "interaction radius". Other geometry's can be invoked for defining an attractor's interaction and membership boundaries (i.e., squares, rectangles, tilted rectangles, ellipses or arbitrary mouse-drawn regions). In general, cluster membership boundaries are chosen to approximate the actual size and shape of their target clusters. Attractor interaction boundaries are chosen that both 1) delimit the scan area where center-of-mass should be found and 2) exclude neighboring clusters from possible interaction.

An attractor can be defined on a subset of arriving parameters. Different attractors may be defined on different subsets of arriving parameters, if useful for clustering their respective populations. A mask, M, or vector of binary switches, is stored within each attractor to signify which parameters of incoming event vectors are to be attended to and which ignored. Since the attractor engine can be defined in any N-dimensional space, it can be defined on a subset of parameters without embellishment beyond the mere requirement to specify M. The vector operations that underlie the attractor engine are implemented in such a way that masked out parameters are treated as non-existent in a completely transparent fashion. The benefits of parameter masking are that it 1) permits data clusters to be defined in the subset of parameters which affords the sharpest cluster definition, 2) allows parameters to be ignored which smear an otherwise well-formed cluster and 3) support classification at varying degrees of dimensional collapse. The latter benefit requires that a single event be permitted to be classified by multiple attractors.

Referring to FIGS. 3A, 3B, 3C, 4A, 4B and 4C, peripheral whole blood was obtained from normal adult volunteers in EDTA containing evacuated blood collection tubes. Erythrocyte were lysed in a lysing solution comprising $NH_4Cl$, $KHCO_3$ and EDTA. The lysed cells were spun down and removed.

The remaining cells were placed in a test tube containing PBS. To this tube were added, in sequence, Leu 4 FITC (anti-CD3; BDIS), Leu 11+19 PE (anti-CD16, CD56; BDIS) and Leu 12 PerCp (anti-CD19; BDIS). These antibodies will label T lymphocytes, NK cells and B lymphocytes respectively. After incubation the cells were washed and then run on a FACScan brand flow cytometer (BDIS) equipped with Consort FACScan Research Software (BDIS). The data was acquired and stored in list-mode. 15,000 events were recorded.

Figure 3A:
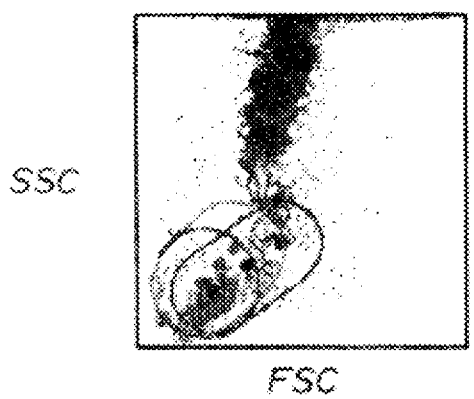
FIGS. 3A, 3B and 3C comprise a series of colored 2-D dot plots of FSC vs. SCC (FIG. 3A), log fluorescence FITC vs. log fluorescence PE (FIG. 3B), and log fluorescence FITC vs. log fluorescence (FIG. 3C) for data collected in list mode from erythrocyte whole blood to which different fluorescently labeled monoclonal antibodies have been added. The three gravitational attractors and their respective seed locations are shown prior to autoclustering. The blue dots and boundaries identify the NK cell attractor; the red dots and boundaries identify B lymphocyte attractor; and the green dots and boundaries identify T lymphocyte attractor.
Figure 3B:
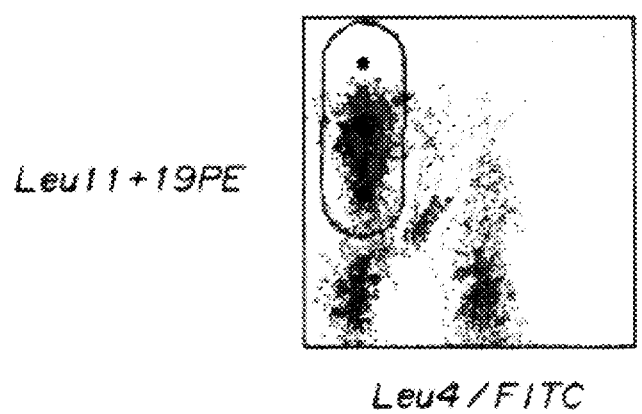
Figure 3C:
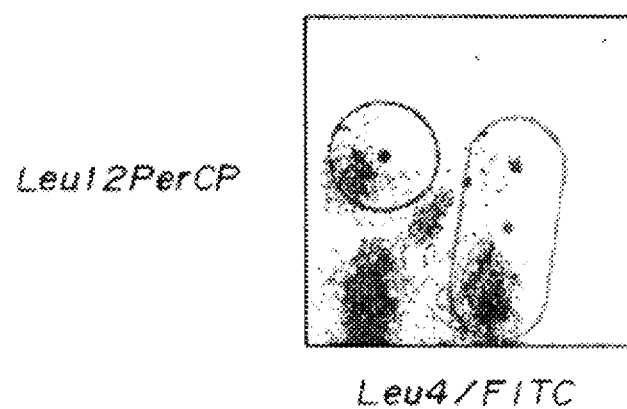

In FIGS. 3A, 3B and 3C, the seed location, s, and radius, r or cr, of each population's attractor was identified prior to analysis based upon well known and published data. A spherical attractor was applied for B lymphocytes while cigar attractors were used for NK cells and T lymphocytes. Each attractor then was mouse drawn to represent the expected locations of each population when the data was analyzed for scatter (FIG. 3A), PE vs. FITC fluorescence (FIG. 3B) and PerCp vs. FITC fluorescence (FIG. 3C). Gray dots are shown interposed on the dot plots showing unclustered events. (In other embodiments, it will be appreciated that these unclustered events need not be displayed in either real time or list-mode analysis.)

Figure 4A:
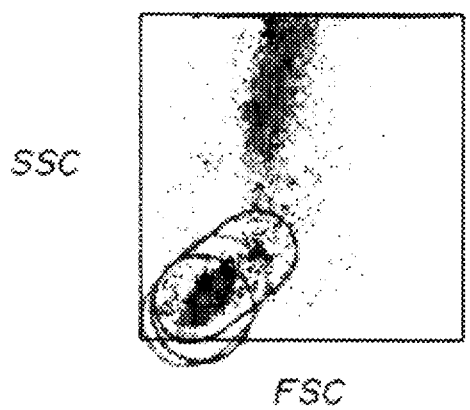
FIGS. 4A, 4B and 4C comprise the colored 2-D dot plots as set forth in FIGS. 3A, 3B and 3C post analysis showing the autoclustered populations and final positions of the attractors. The gray dots represent unclustered events (e.g., monocytes, granulocytes and debris) in the sample.
Figure 4B:
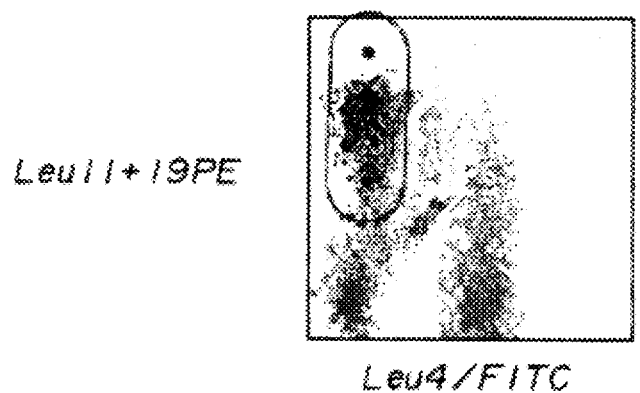
Figure 4C:
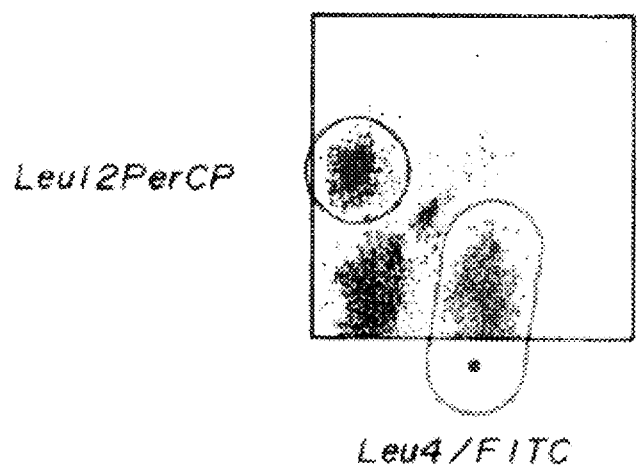

In FIGS. 4A, 4B and 4C, the results of classification are displayed after all recorded events have been analyzed. The parameters measured, and thus included in each event vector, were FSC, SSC, log PE fluorescence, log FITC fluorescence and log PerCP fluorescence. For B lymphocytes, 757 cells (or approximately 19% of all clustered events) were within this cluster. For T lymphocytes, 2596 (or approximately 66% of all clustered events) were within the cluster; and for NK cells, 587 events were within this cluster. It should be appreciated that the data analysis for all of the attractors occurs at the same time. FIGS. 4A, 4B and 4C represent the 2-D projections of each attractor post analysis.

Referring to FIGS. 5A, 5B, 6A and 6B, whole blood was obtained from an AIDS patient (FIGS. 5A and 6B) and from a normal adult volunteer in EDTA containing evaluated blood collection tubes. Each sample was split into two aliquots. A mixture of 50,000 fluorescent microbeads, titered amounts of antibody and buffer to make 400 µl was prepared for each aliquot. To one aliquot from each sample the antibodies consisted of Leu 4 PE/Cy5 and Leu 3a PE. (Cy5 was obtained from Biological Detection Systems.) To the other aliquot from each sample the antibodies consisted of Leu 4 PE/Cy5 and Leu 2a PE. (Leu2a is an anti-CD8 monoclonal antibody available from BDIS.) To the mixture in each aliquot was added 50 µl of whole blood. The aliquots were incubated for 30 minutes, vortexed and then run on a FACSCount brand flow cytometer. Data was acquired and stored in list-mode. A fluorescence threshold was set in the PE/Cy5 channel to exclude the majority of red blood cells, however, care was taken to assure that the threshold was to the left of the far most expected edge of the $CD4^-$ and $CD8^-$ attractors.

Three elliptical attractors were applied to the bead, $CD4^-$ and $CD4^+$ or $CD8^-$ and $CD8^+$ clusters. One difficulty encountered in the analysis of CD8 cells is that, unlike CD4 cells, CD8 cells do not differentiate into well defined positive and negative clusters. A small number of CD8 cells will appear to be "dim." These dim cells are $CD8^+$ and therefore must included in the count if the absolute is to be accurate.

A new clustering tool was developed to solve this problem. A "pipe" is drawn connecting the upper (i.e., $CD8^+$) cluster with the lower (i.e., $CD8^-$) cluster. It is drawn so that in a 2-D plot one side extends from the left most edge of the upper cluster boundary to the left most edge of the lower cluster boundary and the other side extends from right most edge of the upper cluster boundary to the right most edge of the lower cluster boundary. Any events falling within the orbital bands surrounding the cluster boundaries of the pipe are monitored as a PQA check assuring proper containment of $CD8^{dim}$ cells and as a PQA check against encroachment by debris.

In addition the pipe region tool described above, an additional tool was developed to handle the special case where fluorescent control and/or reference beads are included in the analysis of fluorescently labelled cells. In this instance, a circular 2-D bead peak attractor is used to pinpoint the vector mean of the beads, which is then used to predict, by fixed vector offsets, the most likely positions of the cell population clusters. The goal is that the bead peak location will reveal drift in the optical power alignment and sensitivity of the instrument. Any drift in the bead peak predicts similar drift in the cell clusters; therefore, any offset in the location of the bead peak will cause the seed locations to be offset by a similar amount in a similar direction. This may be accomplished by a two-step analysis where only beads are analyzed initially in order to establish the bead peak or by means of analysis of a control tube prior to actual sample acquisition. In the former case, a circular attractor is employed to establish the bead peak while an elliptical attractor is employed in the analysis step.

Figure 5A:
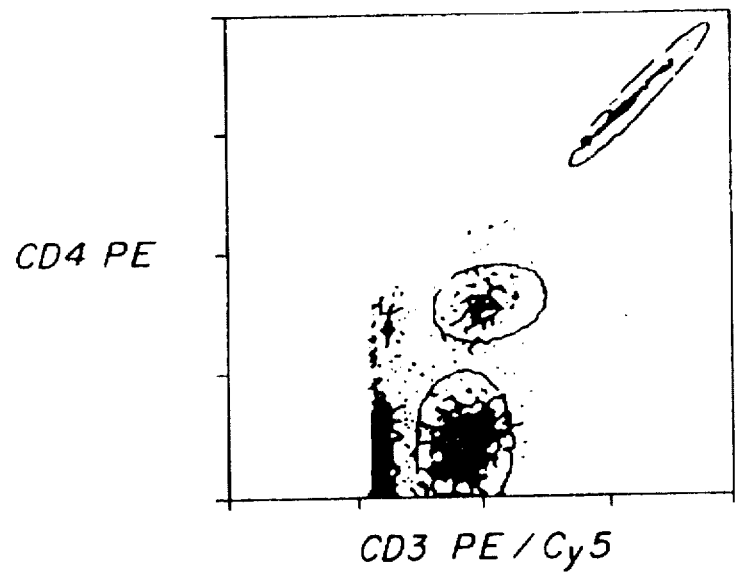
FIGS. 5A and 5B comprise two dot plot of log PE version by PE/Cy5 fluorescence showing three autoclustered populations from a sample of unlysed whole blood from a AIDS patient to which a solution containing a known concentration of fluorescently labeled microbeads and fluorescently labeled (FIG. 5A) anti-CD3 and anti-CD4 monoclonal antibodies or (FIG. 5B) anti-CD3 and anti-CD8 monoclonal antibodies have been added.
Figure 5B:
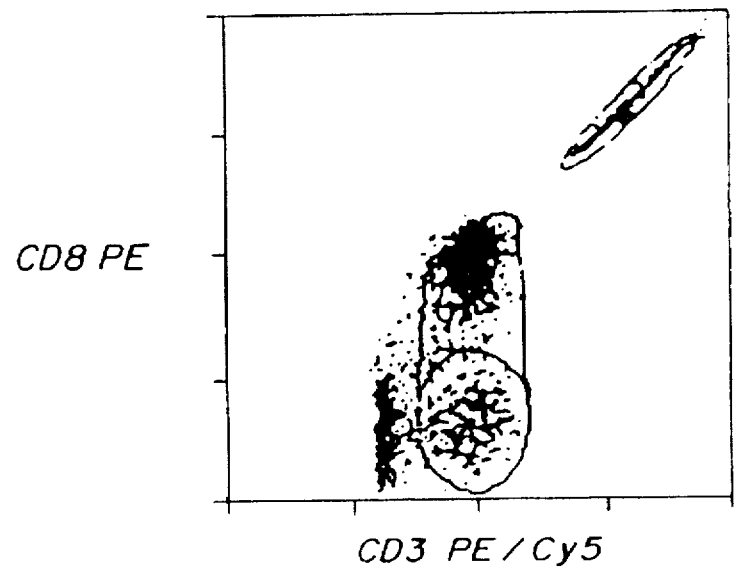

(FIGS. 5A and 5B) display the final positions of the clusters and the events that fell within each cluster for whole blood from an AIDS patient. In FIG. 5A, the majority of events within a cluster occur within the $CD4^-$ or $CD8^-$ clusters. There are few, events that fall outside the cluster that are not either $CD4^+$ or $CD4^-$ T cells or beads. In FIG. 5B, the events are distributed in a manner similar to $CD4^+$ cells; however, the pipe region is applied to collect those $CD8^+$ cells that express "dim" amounts of fluorescence. Table I sets forth the numbers of events that fell within each cluster as well as those non-red blood cell events that were not clustered.

TABLE I

| CD4 Tube | | CD8 Tube | |
|---|---|---|---|
| Beads 6729 | Orb. Beads 4 | Beads 17229 | Orb. Beads 17 |
| $CD4^+$ 874 | Orb. $CD4^+$ 56 | $CD8^+$ 5101 | Orb. $CD8^+$ 426 |
| $CD4^-$ 4579 | Orb. $CD4^-$ 223 | $CD8^-$ 1548 | Orb. $CD8^-$ 227 |
| | | $CD8^{dim}$ 586 | Orb. $CD8^{dim}$ 117 |

Based upon this data, the number of $CD4^+$ cells per µl of whole blood was calculated as 156; the number of $CD3^+$ cells per μl of whole blood was calculated to as 972 in the CD4 tube and 978 in the CD8 tube; and the number of CD8⁺ cells per μl of whole blood was calculated as 769. The number of cells in the orbital bands was low confirming the integrity of the cluster.

Figure 6A:
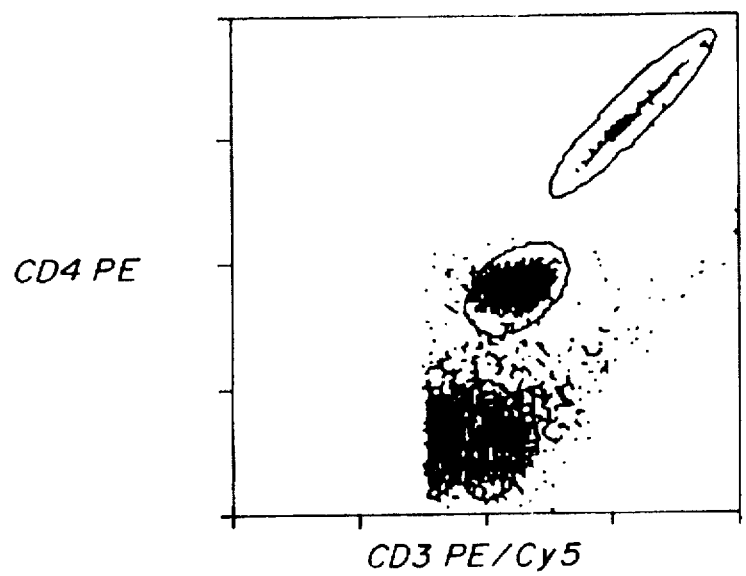
FIGS. 6A and 6B comprise a dot plot as in FIGS. 5A and 5B, however, the blood is taken from a normal individual but the sample has been rejected by PQA.
Figure 6B:
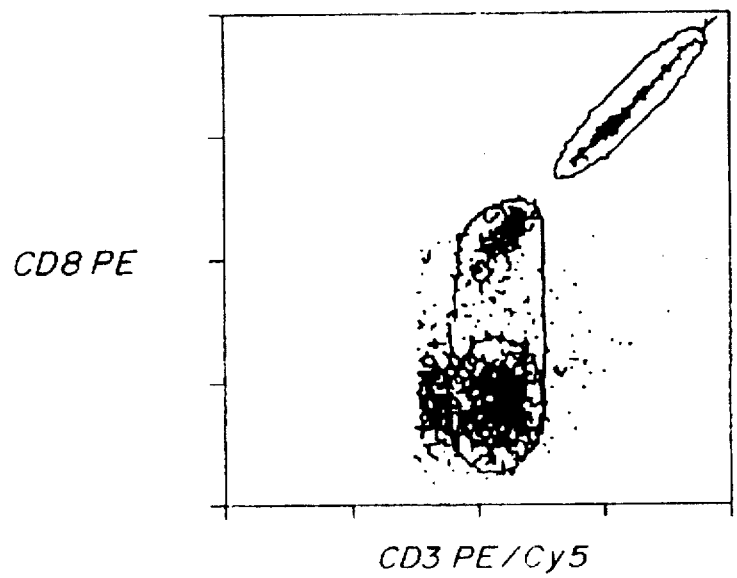

The data from FIGS. 5A and 5B are to be compared with the data from FIGS. 6A and 6B to show how this invention provides PQA. For example, from FIG. 6A it can be seen that the CD4⁻ cluster is contaminated with debris and red blood cells, whereas in FIG. 5A there is a separation between the red blood cells/debris and the CD4⁻ cells. This problem also shows up in Table II where the number of events occurring in the orbital bands for CD4⁻ and CD8⁻ is higher than should be expected if cluster integrity had been maintained. Based on this data, the sample in FIGS. 6A and 6B should have been rejected.

TABLE II

| CD4 Tube | | CD8 Tube | |
|---|---|---|---|
| Beads 9468 | Orb. Beads 1 | Beads 17453 | Orb. Beads 13 |
| CD4⁺ 2501 | Orb. CD4⁺ 69 | CD8⁺ 713 | Orb. CD8⁺ 82 |
| CD4⁻ 1519 | Orb. CD4⁻ 763 | CD8⁻ 2501 | Orb. CD8⁻ 343 |
| | | CD8$^{dim}$ 189 | Orb. CD8$^{dim}$ 173 |

Another aspect of this invention also is shown in Table II. For both the CD4 and CD8 tube, once the number of events that were CD4⁺ exceed 2500, the counting ceased. The instrument had been set with 2500 events in the CD4⁺ window as an auto-shut off. The same is true for the number of CD8⁻ events in the CD8 tube.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. An automated method for classifying particles in at least one sample into one or more data clusters comprising the steps of:

(a) automatically collecting a plurality of parameters for each of a plurality of particles in a sample;

(b) automatically displaying each particle on a set of two-dimensional scatterplots;

(c) manually defining an initial position of at least one variable position, geometric boundary surface on the set of two-dimensional scatterplots so as to enclose a group of the displayed particles in a data cluster;

(d) automatically determining the statistical center-of-mass of the data cluster of particles contained within the geometric boundary surface by means of a gravitational attractor engine; and (e) automatically relocating the position of the geometric boundary surface on the set of two-dimensional scatterplots about the newly calculated statistical center-of-mass for the data cluster of particles.

2. The automated method of claim 1 further comprising the steps of:

(f) automatically repeating steps d)-e) until a user-defined number of particles or all available particles have been included in the calculation of a final center location; and (g) automatically comparing all available particles with the geometric boundary surface for inclusion within or exclusion outside the data cluster associated with the geometric boundary surface.

3. The automated method of claim 2 further comprising the steps of:

(h) automatically repeating steps a)-g) sequentially for one or more additional samples, and wherein the step of manually defining an initial position of the geometric boundary surface is adapted to automatically position the geometric boundary at the initial position.

4. The automated method of claim 1 wherein the step of manually defining an initial position of the geometric boundary surface includes defining size, shape and orientation of the geometric boundary surface.

5. An automated method for classifying particles in at least one sample into one or more data clusters from a flow cytometer comprising the steps of:

(a) automatically collecting a plurality of user selected parameters for each of a plurality of particles in a sample;

(b) automatically displaying each particle on a set of two-dimensional scatterplots;

(c) manually defining an initial position of at least one variable position, geometric boundary surface on the set of two-dimensional scatterplots so as to enclose a group of the displayed particles in a data cluster, with said geometric boundary surface having a user-defined size, shape and orientation;

(d) automatically determining the statistical center-of-mass of the data cluster of particles contained within the geometric boundary surface by means of a gravitational attractor engine;

(e) automatically relocating the position of the geometric boundary surface on the set of two-dimensional scatterplots about the newly calculated statistical center-of-mass for the data cluster of particles;

(f) automatically repeating steps d)-e) until a user-defined number of particles or all available particles have been included in the calculation of a final center location; and (g) automatically comparing all available particles with the geometric boundary surface for inclusion within or exclusion outside the data cluster associated with the geometric boundary surface.

6. The automated method of claim 5 further comprising the steps of:

(h) automatically repeating steps a)-g) for one or more additional samples, and wherein the step of manually defining an initial position of the geometric boundary surface is adapted to automatically position the geometric boundary at the initial position.

7. The automated method of claim 1 further comprising the step of:

(f) automatically repeating steps d)-e) until there are insignificant deviations in the position of the geometric boundary surface.

8. The automated method of claim 5 further comprising the step of:

(h) automatically repeating steps a)-g) until there are insignificant deviations in the position of the geometric boundary surface.

9. A method for classifying a sample of blood cells in a sample of such cells into two or more clusters comprising the steps of:

(a) manually positioning a plurality of geometric boundaries on a series of two dimensional plots in the region where a cluster is expected;

(b) analyzing the cells by means of flow cytometry wherein at least two parameters of data are recorded in real time or from pre-recorded data for each cell analyzed;

(c) displaying each blood cell in the sample of blood cells on a set of two-dimensional plots;

(d) manually defining an initial position of at least one variable position, geometric boundary on the set of two-dimensional plots so as to enclose a group of the displayed particles in a data cluster;

(e) automatically determining the statistical center-of-mass of the data cluster of particles contained within the geometric boundary by means of a gravitational attractor engine; and (f) automatically relocating the position of the geometric boundary on the set of two-dimensional scatterplots about the newly calculated statistical center-of-mass for the data cluster of particles.

10. The automated method of claim 9 further comprising the steps of:

(g) automatically repeating steps e)–f) until (1) a user-defined number of particles has been included in the calculation of a final center location or (2) insignificant deviations occur in the position of the geometric boundary or (3) all available particles have been included in the calculation of a final center location; and (h) automatically comparing all available particles with the geometric boundary for inclusion within or exclusion outside the data cluster associated with the geometric boundary.

11. The automated method of claim 10 further comprising the steps of:

(i) automatically repeating steps a)–h) sequentially for one or more additional samples, and wherein the step of manually defining an initial position of the geometric boundary is adapted to automatically position the geometric boundary at the initial position.

12. The automated method of claim 9 wherein the step of manually defining an initial position of the geometric boundary includes defining size, shape and orientation of the geometric boundary.

13. The automated method of claim 9 wherein the number of clusters is two.

* * * * *